United States Patent [19]

Ragonese et al.

[11] Patent Number: 4,851,606
[45] Date of Patent: Jul. 25, 1989

[54] CONTROL OF WASTE WATER CHEMICAL OXYGEN DEMAND IN AN OXYGENATE TO HYDROCARBON CONVERSION PROCESS

[75] Inventors: Frank P. Ragonese, Cherry Hill, N.J.; Sergei Yurchak, Media, Pa.

[73] Assignee: Mobil Oil Corporation, New York, N.Y.

[21] Appl. No.: 185,751

[22] Filed: Apr. 25, 1988

[51] Int. Cl.$^4$ .............................................. C07C 1/20
[52] U.S. Cl. .................... 585/640; 585/733; 585/639; 210/774
[58] Field of Search ............... 210/622, 623, 774; 565/408, 733, 322, 609, 640; 208/DIG. 1

[56] References Cited

U.S. PATENT DOCUMENTS

| | | |
|---|---|---|
| 2,847,368 | 8/1958 | Worthington et al. ............... 202/46 |
| 3,931,349 | 1/1976 | Kuo .................................... 260/668 |
| 3,998,899 | 12/1976 | Daviduk et al. .................... 260/668 |
| 4,506,106 | 3/1985 | Hsia et al. ....................... 585/640 X |
| 4,627,911 | 12/1986 | Chen et al. ...................... 585/40 X |
| 4,686,312 | 8/1987 | Chu et al. ...................... 585/640 X |
| 4,709,113 | 11/1987 | Harandi et al. ..................... 585/640 |

Primary Examiner—Glenn Caldarola
Attorney, Agent, or Firm—Alexander J. McKillop; Charles J. Speciale; L. G. Wise

[57] ABSTRACT

In a process for converting $C_1$ to $C_4$ oxygenates to hydrocarbons by contacting the oxygenates with a crystalline zeolite conversion catalyst and wherein a byproduct water effluent stream is produced, the improvement which comprises, regulating the operating temperature of a gaseous/liquid hydrocarbon/water phase separator from which said byproduct water effluent stream issues so that the total byproduct water chemical oxygen demand is reduced.

13 Claims, 3 Drawing Sheets

CONTROL OF WASTE WATER CHEMICAL OXYGEN DEMAND IN AN OXYGENATE TO HYDROCARBON CONVERSION PROCESS

FIELD OF THE INVENTION

The present invention relates to the synthetic production of hydrocarbons. More particularly, the present invention relates to a process for the conversion of oxygenates to hydrocarbons. Even more particularly, the present invention relates to an oxygenate to hydrocarbon conversion process wherein the byproduct water stream issued from a product separator in methanol-to-gasoline (MTG) and methanol-to-olefins (MTO) processes contains a decreased chemical oxygen demand (COD).

BACKGROUND OF THE INVENTION

Methods for producing gasoline boiling range hydrocarbons from methanol or other lower aliphatic oxygenates (referred to hereinafter as an MTG process) are generally known, as exemplified in U.S. Pat. Nos. 3,998,899 (Daviduk et al), 3,931,349 (Kuo) and 4,044,061 (Chang et al). incorporated herein by reference. In an MTG process, methanol is quantitatively converted to hydrocarbons and water. The hydrocarbons are primarily gasoline boiling range materials. Gasoline as such term is used in the instant specification and as such term is commonly used in the petroleum industry is useful as a motor fuel for internal combustion engines. More specifically, gasoline is hydrocarbon in nature, being composed of various aliphatic and aromatic hydrocarbons having a full boiling range of up to about to 430° F., depending upon the exact blend used and the time of year. Although gasoline is predominantly hydrocarbon in nature, various additives which are not necessarily exclusively hydrocarbon are often included. Additives of this type are usually present in very small proportions, e.g., less than 1% by volume of the total gasoline. It is also not uncommon for various gasolines to be formulated with non-hydrocarbon components, particularly alcohols and/or ethers as significant, although not major constituents thereof. Such alcohols, ethers and the like have burning qualities in internal combustion engines which are similar to those of hydrocarbons in the gasoline boiling range. For purposes of this application, the term "gasoline" is used to mean a mixture of hydrocarbons boiling in the aforementioned gasoline boiling range and is not intended to mean the above-referred to additives and/or non-hydrocarbon constituents.

In the basic MTG process, methanol or other $C_1$ to $C_4$ aliphatic oxygenates contained in the feedstock are essentially dehydrated, with gasoline and water given off as the primary products. The intermediate-size zeolite catalysts suitable for use in the MTG process, such as ZSM-5, are selectively penetrated by molecules of intermediate size and are thus capable of converting lower aliphatic oxygenates such as methanol, into high octane gasoline. Gasoline selectivity is considered to be extremely high in the MTG process using this type of intermediate pore size catalyst, described in further detail below, because the sizes of the channels are just wide enough to produce hydrocarbons boiling in the gasoline range. That is, the reaction product terminates at about a carbon number of 10.

The conversion of methanol to gasoline boiling range hydrocarbons is accompanied by the formation of substantial amounts of water byproduct, which contains trace levels of oxygenated compounds (about 0.1–0.2 wt %). This water prduct is sent to a waste water treatment plant to reduce the concentration of oxygenates to acceptable limits.

U.S. Pat. No. 2,847,368 discloses a process for the extraction of hydrocarbons from an aqueous medium to obtain a purified water stream. The extraction is conducted in a column and at a temperature of about 100° C. Further, U.S. Pat. No. 3,998,899 (Daviduk et al) refers to an embodiment in an MTG process wherein the separator drum shows a temperature of about 100° F. (about 38° C.) to provide a rough separation of a cooled hydrocarbon-containing effluent into a water phase, a hydrocarbon phase and a gaseous phase. U.S. Pat. No. 3,931,349 (Kuo et al) also discloses prior art separator conditions in an MTG process wherein heat exchange arrangements may contribute to reducing the reactor temperature effluent to about 100° F. (about 38° C.) before entry into a low pressure separator maintained at a temperature of about 100° F. as well. Gasoline boiling components thus separated and recovered may further be separated in a high pressure separator operated at an unspecified temperature.

In practical operation of MTG and MTO process, however, the product separator temperature fluctuates depending upon the cooling water temperature which varies day to night, week to week, etc., depending on the air temperature. In other words, in normal practice the product separator temperature is not controlled at all.

Methods for converting methanol, dimethylether (DME) and other lower aliphatic oxygenates, such as alcohols or corresponding ethers, to olefins using medium pore size zeolite catalysts (referred to hereinafter as an MTO, methanol-to-olefins, process) are also generally known, as exemplified in U.S. Pat. No. 4,543,435 (Gould et al), incorporated herein by reference. In an MTO continuous process, olefinic hydrocarbon products are produced by the catalytic conversion of the oxygenate feedstock to an intermediate lower olefinic stream. This primary phase catalytic reaction also results in the formation of a byproduct waste water effluent stream upon phase separation from the hydrocarbon phase containing a major amount of $C_2$–$C_4$ olefins. Thereafter, the thus-produced olefins can be oligomerized to produce distillate and gasoline, with recovery of an ethene-rich gaseous phase for recycle to the primary catalytic stage, if desired. For example, the olefinic feedstock can be converted to $C_5^+$ gasoline, diesel fuel, etc. Representative conversion processes for the olefinic feedstock produced in the primary MTO process include the Mobil Olefins to Gasoline/Distillate (MOGD) method referred to by Gould et al, as well as a method for converting $C_2$–$C_5$ olefins, alone or in admixture with paraffinic components into higher hydrocarbons over crystalline zeolites having controlled acidity. The Gould et al patent refers to specific patents directed to these various olefin-to-gasoline methods.

However, in byproduct water streams produced upon operation of MTG and MTO processes, the amount of oxygenate components, contained therein is undesirably high, and in practice, waste water treatment plants must devote valuable resources to reducing the oxygenate content and COD to environmentally acceptable limits.

SUMMARY OF THE INVENTION

Accordingly, one object of the present invention is to significantly improve a continuous process for converting lower aliphatic oxygenated hydrocarbon feedstock to liquid hydrocarbons, byproduct water and light gas by reducing the total waste water COD.

Another object of the present invention is to reduce the size of waste water treatment plants to be used for the treatment of an oxygenate to hydrocarbon conversion process waste water effluent, and to conserve treatment plant resources.

Still another object of the present invention is to minimize the potential for upsetting the waste water treatment plant due to high quantities of oxygenates in the waste water, and to effectively eliminate the possibility of environmental discharge of unacceptable quality effluent in terms of COD.

These and other objects of the present invention are satisfied by a process for converting lower aliphatic oxygenated hydrocarbon feedstock to liquid hydrocarbons wherein a byproduct water stream is produced by contacting the feedstock with a conversion catalyst, comprising regulating the operating temperature of a gaseous/liquid hydrocarbon/by-product water phase separator from which said byproduct water effluent stream issues to reduce the total byproduct water chemical oxygen demand.

Preferably, the process for converting lower aliphatic oxygenated hydrocarbon feedstock to liquid hydrocarbons, byproduct water and light gas, comprises the steps of (a) contacting the oxygenate feedstock in a reaction zone with a conversion catalyst at elevated temperature and pressure to produce a hot effluent vapor stream containing $C_5+$ gasoline boiling range hydrocarbons, light hydrocarbons and water; (b) cooling the effluent stream under pressure to condense a major amount of $C_5+$ hydrocarbons as a liquid phase along with a byproduct aqueous phase containing dissolved organic components; and (c) separating the cooled effluent stream at a temperature greater than 40° C. to minimize concentration of the organic components in the aqueous phase, while recovering a liquid hydrocarbon stream and a light gas stream.

It is more preferred that the separation step (c) is conducted at a temperature of about 50° C. to 100° C. and at a pressure of at least about 100 kPa to produce a byproduct aqueous phase consisting essentially of water and less than 2000 ppm organic oxygenates.

DETAILED DESCRIPTION OF THE INVENTION

In accordance with the process of the present invention, controlling the product separator temperature, and controlling the separator pressure in preferred embodiments, has unexpectedly been determined to greatly influence the quantity of organic oxygenates in the raw waste water effluent. Thus, practice of the process of the present invention desirably results in a reduced size of the waste water treatment plant and effectively eliminates the possibility of discharge of unacceptable quality effluent as to COD because space and resources that are presently used to reduce waste water COD are conserved. The magnitude of this decrease in the total waste water COD is considered to be quite unexpected, considering the fact that the organic oxygenate content of the waste water entering the product separator is less than about 0.2 wt %. Thus, by controlling the product separator temperature (and pressure in preferred embodiments), in accordance with the process of the present invention, the waste water treatment facilities needed for the MTG and MTO oxygenate to hydrocarbon conversion processes can be substantially reduced in size, and the risks of discharging to the environment unacceptable quality effluent are also largely minimized. Also, since biological oxygen demand (BOD) is generally a function of COD the process of the present invention also desirably reduces the total waste water BOD.

It is contemplated that any $C_1$ to $C_4$ oxygenates, such as monohydric alcohols having from 1 to 4 carbon atoms, or ethers derived from these alcohols may be used as feed to the process of this invention. Thus, methanol, ethanol, n-propanol, iso-propanol, n-butanol, sec-butanol and iso-butanol may be used either alone or in admixture with one another. Likewise, mixed ethers derived from these alcohols such as methyl-ethylether, may similarly be used. Particularly preferred feeds are methanol, dimethylether and mixtures thereof. Such $C_1$-$C_4$ oxygenates also include suitable ketones, aldehydes, etc. At some portions of the following description of the present invention methanol will be used as a representative example of a $C_1$ to $C_4$ oxygenate suitable as the feed material.

The $C_1$ to $C_4$ oxygenates may be used in conjunction with water as the feedstock, if desired in proportions rangin from about 0 to about 50% by weight.

Although the chemistry of the MTG process is quite complex it will be briefly explained hereafter in simple terms. Methanol can be considered to consist of a hydrocarbon-like part and a water-like part. In the MTG process, the methanol is essentially dehydrated, with gasoline and water as the primary products. The zeolite catalyst, described in detail hereafter, wrings out the water from the methanol, and rearranges the hydrocarbon part into high octane gasoline. For every one hundred tons of methanol converted, 44 tons of hydrocarbons and 56 tons of water are formed, according to the stoichiometric yield. Approximately 85–90% of the hydrocarbon product is high quality gasoline. The energy balance of the process is extremely favorable; about 95% of the thermal energy of the methanol feed is preserved in the hydrocarbon product. Water, of course, has no thermal energy as a fuel and the remaining 5% escapes as heat of reaction. The overall energy efficiency of the MTG process, including processing energy, is also very high at about 92-93%.

The initial step in this transformation is the reversible dehydration of methanol to dimethylether. These two oxygenates then dehydrate further to give light olefins, which in turn react to form heavier olefins. Finally, the olefins rearrange to paraffins, cycloparaffins and aromatics. Almost no hydrocarbons are found higher than $C_{10}$ due to the shape selective nature of the zeolites used in accordance with the present invention.

Figure 1:
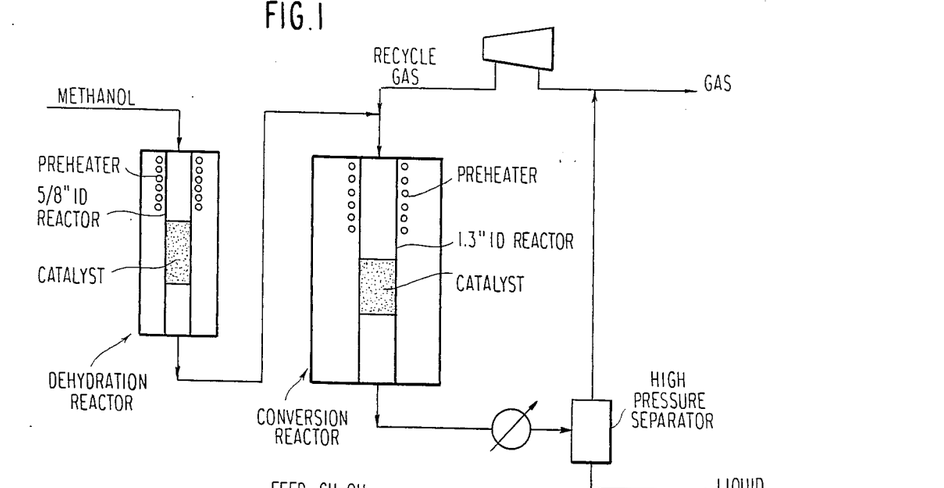
FIG. 1 is a schematic of a standard fixed-bed MTG process configuration which may be used in the process of the present invention, showing a dehydration reactor, conversion reactor and high pressure separator through which the effluent from the conversion reactor flows.

In an adiabatic fixed-bed MTG process illustrated schematically in FIG. 1, methanol is first dehydrated to an equilibrium mixture of methanol, dimethylether and water in a dehydration reactor ($2CH_3OH \rightleftharpoons (CH_3)_2O + H_2O$). This reaction takes place in either conversion of methanol to gasoline (MTG) or to lower olefins (MTO). This equilibrium mixture is then diluted with recycle gas and converted to hydrocarbons and water over the zeolite catalyst in a conversion reactor. The recycle gas, which is comprised primarily of light hydrocarbon products (e.g. methane, ethane, propane) provides mass to absorb the heat of reaction and thereby reduce the temperature rise in the conversion reactor to a manageable level. About 20 and 80 percent of the total heat of reaction is released in the dehydration and conversion reactors, respectively. The reactor effluent is cooled and partially condensed, and the aqueous, liquid hydrocarbon and gaseous phases are separated, with most of the gas being recycled. The separation step will be described in greater detail hereinafter. The adiabatic fixed-bed MTG process operates at essentially 100% conversion of methanol to hydrocarbons and water until the catalyst deactivates by carbon formation thereon to an activity level such that only partial conversion of methanol is achieved. When unconverted methanol (e.g. 0.1 weight percent) appears in the aqueous phase product the catalyst has been deactivated to the point where "methanol breakthrough" occurs. In other words, methanol breakthrough can be defined as the point at which 99.9% methanol conversion or less is achieved. This term is to be understood as inclusive of any $C_1$ to $C_4$ oxygenate, even though defined in terms of the preferred feed, methanol.

In the conventional MTG process, at this stage, i.e., methanol breakthrough, the normal practice is to regenerate the conversion catalyst, such as ZSM-5, by burning the coke having formed on the catalyst with dilute oxygen, followed by the reactor being re-streamed with the feedstock. Cycle lengths between ZSM-5 catalyst regenerations are typically 20 days. However, the dehydration reactor, employing (e.g., $\gamma$-alumina catalyst) may operate for over a year without regeneration.

Figure 2:
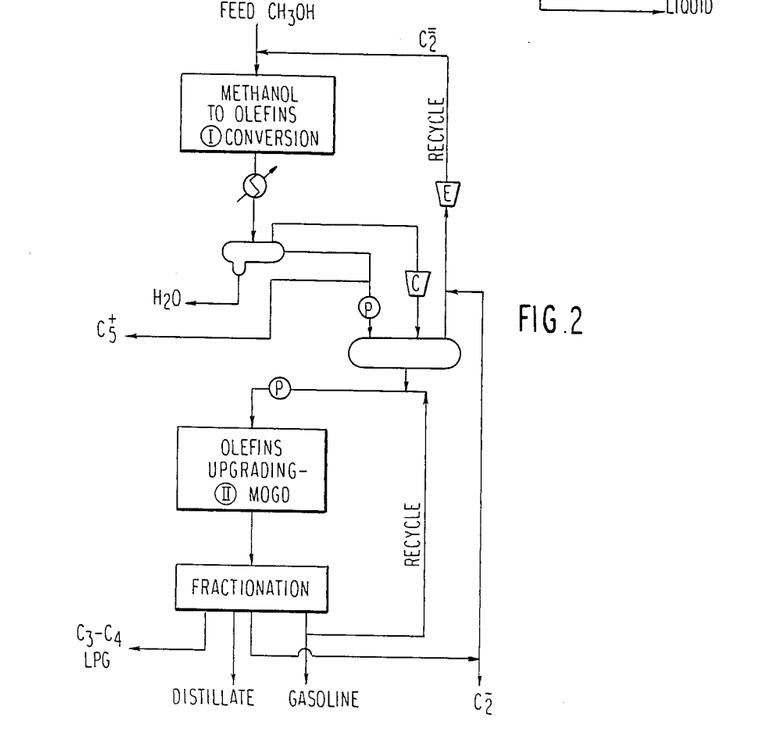
FIG. 2 is a process flow sheet showing the major unit operations and process streams in a representative MTO-type process (Stage I) to which the present invention is applicable, and also shows major steps in a representative olefin upgrading (MOGD, Stage II) process.

Referring to FIG. 2 depicting the major steps in an MTO process, the oxygenate feedstock (methanol or DME, for instance) is fed to the primary stage I (MTO) reactor where the feedstock is contacted with a conversion catalyst and converted to lower olefins and gasoline range hydrocarbons plus byproduct water by dehydration of the oxygenate feedstock. Byproduct water is recovered by simple phase separation from the cooled effluent, and this separation step will be described in greater detail hereinafter with reference to typical phase separation conditions in accordance with the present invention. Liquid hydrocarbons from the primary stage I reactor comprising a major amount of $C_2$-$C_4$ olefins and a minor amount of $C_5^+$ gasoline range materials may be recovered or pumped to the higher secondary stage pressure. Ethene is usually recycled to the primary stage. At least a portion of the vapor phase effluent from the primary stage is compressed and heated along with the gasoline diluent or other liquids to oligomerization reaction temperature, and the combined olefinic stream (optionally containing recycled olefinic gasoline) is reacted at high pressure and elevated temperature over the secondary stage catalyst. Secondary stage II effluent is then separated into light gases, $C_5^+$ gasoline for recycle in part and distillate range hydrocarbons. The distillate stream comprises a major fraction of $C_{10}$-$C_{20}$ high boiling aliphatics and may contain a minor amount of aromatics.

Catalyst versatility permits the same type of medium pore size crystalline zeolite to be used in both the primary conversion stage (MTO) and secondary oligomerization stage. Likewise the same type of zeolite can be used in both the dehydration and conversion stages in the MTG process. The class of zeolites useful in each of these conversion zones will be described in detail below.

Recent developments in zeolite technology have provided a group of medium pore siliceous materials having similar pore geometry. Most prominent among these intermediate pore size zeolites is ZSM-5 which is usually synthesized with Bronsted acid active sites by incorporating a tetrahedrally coordinated metal, such as Al, Ga, B or Fe, within the zeolitic framework. Medium pore size aluminosilicate zeolites are favored for acid catalysts; however the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,886 (Argauer, et al.), incorporated by reference.

The oligomerization catalysts preferred for use herein include the medium pore (i.e., about 5-7 A) shape-selective crystalline aluminosilicate zeolites having a silica-to-alumina ratio of at least about 12, a constraint index of about 1 to 12 and significant Bronsted acid activity. The method by which constraint index is determined is fully described in U.S. Pat. No. 4,016,218, incorporated herein by reference. In the primary stage (MTO) reactor or a fluid-bed MTG reactor, the coked catalyst preferably has a relatively low acid activity (alpha value) of about 0.1 to 20 under steady state process conditions to achieve the required degree of reaction severity. The secondary stage (MOGD) or fixed-bed MTG catalyst is generally more active (e.g. - alpha value of 10-200 or higher). Representative of the ZSM-5 type zeolites are ZSM-5, ZSM-11, ZSM-12, ZSM-22, ZSM-23, ZSM-35 and ZSM-48. ZSM-5 is disclosed in U.S. Pat. No. 3,702,886 and U.S. Pat. No. Re. 29,948. Suitable zeolites are disclosed in U.S. Pat. Nos. 3,709,979; 3,832,449; 4,076,979; 3,832,449; 4,076,842; 4,016,245; 4,397,827; and 4,542,252 (MTG). The disclosures of these patents are incorporated herein by reference. While suitable zeolites having a coordinated metal oxide to silica molar ratio of about 20:1 to 200:1 or higher may be used, it is advantageous to employ a standard aluminosilicate ZSM-5 having a silica:alumina molar ratio of about 15:1 to 70:1, suitably modified. A typical zeolite catalyst component having Bronsted acid sites may consist essentially of crystalline aluminosilicate having the structure of ZSM-5 zeolite with about 5 to 95 wt. % silica, clay and/or alumina binder.

These siliceous zeolites may be employed in their acid forms ion exchanged or impregnated with one or more suitable metals, such as Ga, Pd, Zn, Ni, Co and/or other metals of Periodic Groups III to VIII. Ni-exchanged or impregnated catalyst is particularly useful in converting ethene under low severity conditions. The zeolite may include other components, generally one or more metals of group IB, IIB, IIIB, VA, VIA or VIIIA of the Periodic Table (IUPAC). Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g., ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone. Certain of the ZSM-5 type medium pore shape selective catalysts are sometimes known as pentasils. In addition to the preferred aluminosilicates. the borosilicate, ferrosilicate and "silicalite" materials may be employed.

ZSM-5 type pentasil zeolites are particularly useful in the process because of their regenerability long life and stability under the extreme conditions of operation. Usually the zeolite crystals have a crystal size from about about 0.01 to over 2 microns or more. with 0.02-1 micron being preferred. In the description of preferred embodiments for fixed-bed MTG or secondary stage (MOGD). catalyst particles may consist essentially of 65% H-ZSM-5 catalyst contained within an alumina matrix and having a fresh alpha value of about 150-200, based on total catalyst weight. A "standard" catalyst is 70:1 aluminosilicate H-ZSM-5 extrudate havin an acid value of at least 20, preferably 150 or higher.

The preferred catalysts of this invention are those comprising zeolites having a constraint index of about 1 to 12 and a silica-to-alumina ratio of at least about 12, preferably about 20:1 to 100:1.

A matrix binder can be employed with the zeolite conversion catalysts in any of the reaction zones used in an MTG or MTO process. The zeolite catalyst can be incorporated, combined, dispersed, or otherwise intimately admixed with the matrix in such proportions that a resulting product will contain from 1% to 95% by weight and preferably from 10% to 70% by weight of the zeolite in the final catalyst composite. For fixed-bed MTG reactors and secondary stage (MOGD) reactors a most preferred ratio is 65% by weight zeolite catalyst to 35% by weight matrix binder. The matrix may include a suitable inorganic composition with which the zeolites can be incorporated, combined dispersed, or otherwise intimately admixed wherein the matrix may be alumina and inorganc oxides, especially those comprising alumina. Of these matrices, inorganic oxides such as clays, silica, silica-alumina, etc., as well as alumina, are particularly preferred because of their superior porosity, attrition resistance and stability.

The conversion reaction zones utilized in the process may be any of a fixed, fluidized or fluid transport type catalyst bed arrangement, which are generally known in the art. A heat exchanger type tubular reactor configuration may also be employed if desired. Appropriate heat exchange apparatus may be provided both within and outside the catalyst bed as desired or required by the particular reactor design. The process of this invention may be accomplished with a catalyst system containing a single catalyst bed, or a plurality of sequentially arranged catalyst beds. It is to be understood that the process of the present invention may be carried out in a catalyst system employing one or more fixed beds of the catalyst, a fluid catalyst system, or a combination thereof. Each bed of catalyst may be contained in a single or separate reactor and the reactors sequentially connected by suitable piping means or other form of passageway for passage of the feedstock and a reaction product mixture thereof downstream from one catalyst bed to the other. On the other hand where a plurality of catalyst beds are employed, they all may be contained in a single reactor of the same or increasing bed thickness in the direction of flow to assist with controlling exothermic reaction heat. Still further, where multiple conversion reactors are employed, each reactor itself may contain multiple catalyst beds in series. For example, embodiments wherein multiple parallel primary stage reactors are used to feed multiple parallel ZSM-5 type conversion reactors, each reactor itself containing a series of catalyst beds, are within the scope of the present invention. Transport type catalyst beds which may be used include those employed in fluid catalytic cracking.

The conversion of methanol to gasoline boiling components is a highly exothermic reaction releasing approximately 750 BTU of heat per pound of methanol (1.74 MJ/kg of methanol). This amount of heat release will result in an adiabatic temperature increase of about 650° C. for pure methanol feed. In an adiabatic catalyst bed reactor, this large temperature increase will result in high catalyst aging rates, and possibly cause thermal damage to the catalyst. Furthermore such high temperatures could cause an undesirable product distribution to be obtained. Therefore, it is critical to the conversion of methanol to useful products to provide sufficient heat removing or dissipating facilities, particularly during initial contact with the crystalline zeolite conversion catalyst, so that the maximum temperature encountered in any portion of the zeolite catalyst conversion step is below an upper predetermined limit.

With respect to the conduct of the desired methanol conversion reaction in an MTG process, the temperature thereof is at least about 315° C. Temperatures up to about 485° C. may also be employed, but preferably the adiabatic reactor effluent temperatures are maintained below about 455° C. for the production of gasoline boiling materials. The pressure may be from about atmospheric up to several thousand kilo Pascals pressure but preferably below about 3500 kPa. The weight hourly space velocity (WHSV) of the methanol charged is within the range of about 0.5 to 1000. It will be understood, of course, that in an embodiment of the invention involving multiple injection of methanol feed in the direction of reactant flow, each introduction of liquid methanol into the reaction products in the catalyst system will effect a temperature control and increase the space velocity thereof downstream from the point of entry.

In an MTO conversion process, olefin production is optimized in the primary stage by employing fluid bed conditions in the temperature range of about 425° C. to 550° C., a pressure range of about 100 to 800 kPa and a catalyst and methanol equivalent in the primary stage feedstock. The secondary stage MOGD process preferably employs a fixed bed of ZSM-5 type catalyst to oligomerize olefins at a temperature of about 190° C. to 315° C. and a pressure of about 4200 to 7000 kPa. Further details of the MTO type process for converting lower aliphatic oxygenates to olefins by dehydration whereby a waste water effluent stream is produced from the primary stage reactor are described in U.S. Pat. No. 4,543,435 (Gould et al) mentioned above, incorporated herein by reference.

The reaction mixture recovered from the conversion catalyst reactor in an MTG process will contain aliphatic and aromatic gasoline boiling range hydrocarbons, lighter aliphatic hydrocarbons and water. As noted above, this reactor effluent also contains some unreacted methanol or unreacted oxygenated compounds or intermediates and hydrocarbons boiling above the gasoline boiling range. In an MTO primary stage process, the effluent from the primary stage reactor contains a major amount of lower olefins and liquid hydrocarbons consisting essentially of $C_5+$ gasoline range materials in addition to byproduct water. The present invention is particularly concerned with product phase separation of the MTG conversion reactor effluent and MTO primary stage reactor effluent. Product recovery may be by a series of unit operations with a relatively simple condensation and phase separation by gravity to separate a gaseous phase, a liquid hydrocarbon phase and an aqueous (byproduct water) phase from each other. This condensation arrangement is suitably accomplished in heat exchange relation with cold methanol feed to heat the cold feed to a predetermined and desired elevated temperature prior to entry into the conversion zone in either the MTG process or a primary stage MTO process. See FIG. 4. U.S. Pat. No. 3,931,349 (Kuo et al), referred to above, discloses typical prior art cooling steps in an MTG process to reduce the temperature of the product effluent before being separated into gaseous, water and liquid hydrocarbon phases in a low pressure separator used in combination with a high pressure separator. This Kuo patent is incorporated by reference, and the heat exchange and separator steps described in detail therein could be followed in practicing the present invention. Alternatively, the condensation arrangement could be accomplished by heat exchange of recycled gas with reactor effluent. See FIG. 3. The final temperature of the reaction product mixture from the MTG conversion reactor or MTO primary stage reactor could also be achieved by means of air or water cooling (see FIG. 3) or a combination of these.

Figure 3:
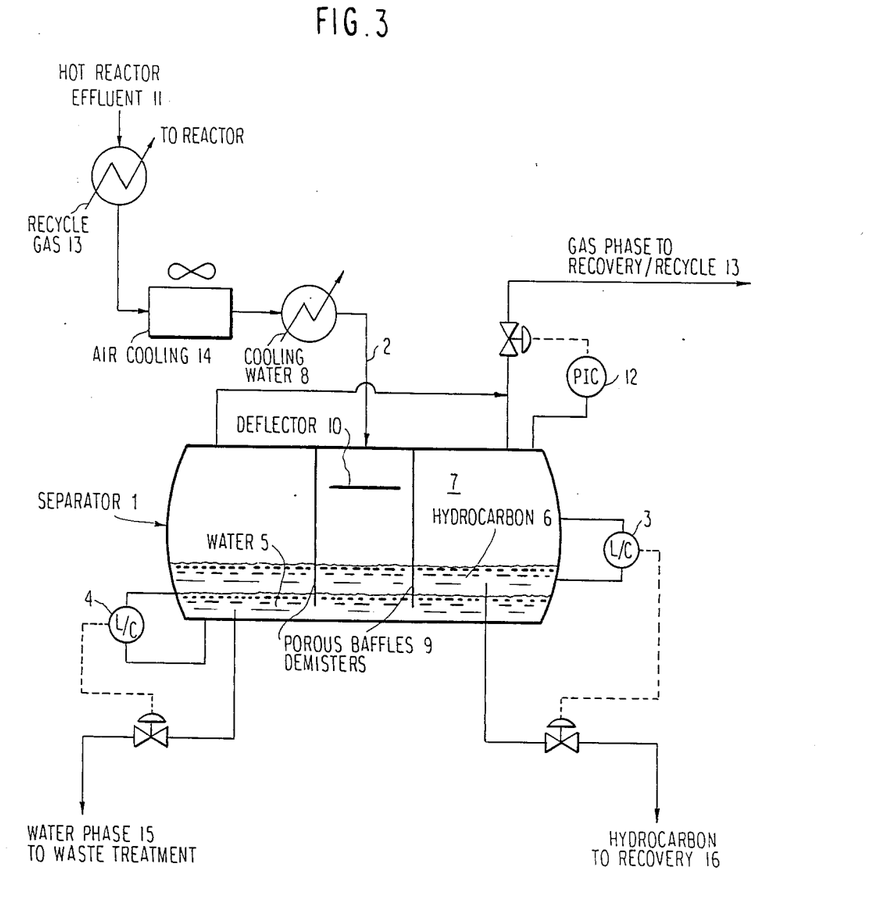
FIG. 3 is a schematic view of a center-entering type product separator design with level control by pneumatic instruments useful in accordance with the present invention.
Figure 4:
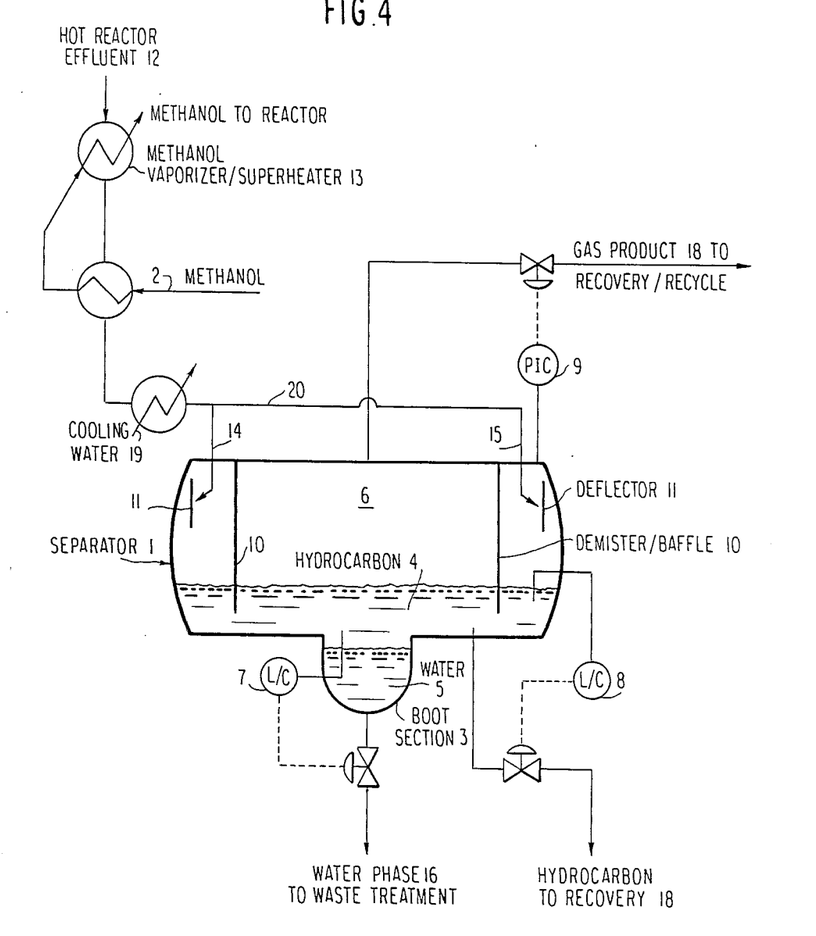
FIG. 4 shows a multiple-end entering product separator design with a boot section for water/hydrocarbon phase separation. Level control is obtained by capacitance probe instruments.

Preferably, a product separator design as shown in FIGS. 3 or 4 is used to separate the gaseous, liquid hydrocarbon and byproduct water phases which make up the reaction product mixture from the MTG conversion reactor or MTO primary stage reactor. In FIG. 3, the hot reactor effluent (11) from the MTG conversion reactor or MTO primary stage reactor passes through conduit means (2) where heat exchange of recycle gas (13) with the reactor effluent may take place. The thus cooled reactor effluent then continues through conduit means (2), and may be further heat exchanged by means of air cooling (14) or water cooling (8). Any of these reactor effluent cooling methods (recycle gas, air cooling or water cooling) may be employed alone or in combination. In FIG. 3, the cooled reactor effluent continues through conduit means (2) into a center-entering separator vessel (1). The effluent contacts a deflector (10), and internal separator flow is regulated by porous baffles or demisters (9). The separator may employ pneumatic instruments (3) and (4) for level control of the three phases. In the interior of the separator vessel, the byproduct water (5) will separate from the liquid hydrocarbon phase (6) by gravity, and the gaseous phase (7) will naturally rise above the liquid and aqueous phases. The product separator temperature may be controlled by automatic or manual control of the cooling water flow, for example. throttling the flow of cooling water to raise the internal separator temperature to a desired level or otherwise regulating the temperature of the reactor effluent as it enters the internal portion of the separator. Means (12) for controlling the pressure during phase separation may also be provided. The gaseous phase is recovered and/or recycled in part (13), and the liquid hydrocarbon stream (16) is sent to conventional petroleum fractionators for separation and stabilization in the MTG process, and may be passed through conduit means ultimately with or without fractionation to the secondary stage MOGD type reactor in an MTO process. The byproduct aqueous phase (15) is sent to a waste water treatment plant. Further the aqueous phase is usually degassed via pressure letdown prior to processing in the treatment plant.

FIG. 4 represents an alternative preferred separator design. In FIG. 4, the hot reactor effluent (12) from the MTG conversion reactor or MTO primary phase reactor is passed through conduit means (20) through a heat exchange relationship with cold methanol feed (2), which is itself heated by the hot reactor effluent and also passed through a methanol vaporizer/superheater (13) before being fed to the dehydration reactor. Cooling water means (19) as in the design illustrated in FIG. 3 may also be present, if desired. In FIG. 4, the thus cooled reactor effluent enters the separator through multiple conduits (14, 15) stationed at the ends of the separator vessel (1). Level control of the water and liquid hydrocarbon phases is obtained by capacitance probe instruments (7) and (8). The effluent enters the separator and first contacts a deflector (11). A pair of porous baffles or demisters (10) is also provided inside the separator vessel, similar to the separator vessel design shown in FIG. 3. The separator vessel itself has a boot section (3) for water (5)/hydrocarbon (4) separation. The gaseous phase (6) naturally remains above the liquid hydrocarbon and water phases in the upper portion of the separator vessel. Trim control of the separator temperature could be obtained by regulating the cooling water flow as in the separator design discussed in FIG. 3, or by air cooling (not shown). The bulk of reactor effluent cooling in the design in FIG. 4 is achieved by preheating/vaporizing/superheating methanol in relation with the hot reactor effluent. If the process in operation is fixed-bed MTG, this could be recycle gas in place of methanol or a combination of recycle gas and methanol. If the process is fluid-bed MTG or MTO primary stage, it could be methanol, as shown in FIG. 4, or steam generation followed by air-/water trim cooling. This same type of trim control would also be understood by one of ordinary skill in the art to be applicable to the separator design discussed above in FIG. 3. Means (9) for controlling the pressure during phase separation may also be provided. Further, as in FIG. 3, the gaseous phase (18) is recovered and/or recycled in part, the liquid hydrocarbon phase (17) is recovered and part or all of it may undergo upgrading in an MOGD type process, and the aqueous water phase is usually degassed by a pressure letdown prior to processing in the waste water treatment plant.

While the two separator designs discussed above and depicted in FIGS. 3 and 4 are preferred for product separation in accordance with the present invention, these arrangements are not mutually exclusive, and it will be understood that other arrangements or combinations are feasible.

A product separator of the type discussed above has been operated at temperatures of about 25°–38° C. (80°–100° F.) in an MTG process or when separating the reaction products from a primary stage MTO reactor, but as noted above this temperature range would simply be the result of fluctuations in the cooling water temperature which varies over time and is dependent, to some extent, on the surrounding air temperature. In the MTG and primary stage MTO process, the waste water which is separated from the gaseous and liquid hydrocarbon phases in the product separator contains trace levels of organic oxygenated components. These are mostly dissolved oxygenated compounds (about 0.1–0.2 wt. %), comprising both acidic and non-acidic oxygenates. In accordance with the present invention, it has now been determined that by controlling or regulating the product separator temperature and pressure under more or less constant process conditions, the total waste water product COD can be decreased by up to 50% or more from the total waste water COD produced in such conventional processes. The magnitude of this decrease in waste water COD is considered to be quite surprising in view of the fact that the oxygenate content, as noted above, of the waste water is usually less than 0.2 wt. % in processes not employing the improved process of the present invention.

Various means can be employed to control or regulate the product separator temperature depending on the particular design used (such as by regulating the hot reactor effluent cooling prior to entry into the separator vessel by adjusting the amount of cooling water, air cooling or controlling the preheating/vaporizing-/superheating of methanol). The effects of the present invention are obtained at product separation temperatures of about 40° C. and above. Also controlling the product separator pressure contributes to the reduced waste water COD. In this regard, a separator pressure of at least 100 kPa is preferred for fluid-bed MTG runs and MTO runs, while higher pressures of at least 900 kPa are preferred for fixed-bed MTG runs. While there is no particular upper limit on the product separator temperature the temperature is preferred to be within the range of 50° C. to 100° C. to achieve the objects of the present invention. The byproduct waste water phase preferably consists essentially of water and less than 2000 ppm organic oxygenates (excluding methanol and/or other feed oxygenates) in accordance with the present invention.

The present invention is hereafter illustrated by reference to the following specific example. However, this example should not be construed as limiting the scope of the present invention in any manner whatsoever.

EXAMPLE 1

A continuous fixed-bed process was operated in a configuration comprising feeding synthetic crude methanol (83 wt. % methanol/17 wt. % water) into a dehydration reactor containing γ-alumina catalyst, mixing the dehydration reactor effluent with recycled light hydrocarbon gas, and passing the mixture into a conversion reactor containing a ZSM-5 type catalyst. A portion of the resulting conversion reactor effluent was condensed in a high pressure separator, which effectively separated a liquid hydrocarbon product, an aqueous water product and a gaseous product. A majority of the uncondensed reactor effluent was recycled back to the conversion reactor inlet. The basic process conditions are shown in Table 1 below.

The product separator temperature was adjusted under otherwise constant process conditions (shown in Table 1), and the composition of the waste water product was determined. From the composition thus-determined, the chemical oxygen demand (COD) was calculated by standard methods. The results of this experiment are shown in Table 2 below:

TABLE 1

| Process Conditions | |
| --- | --- |
| Methanol feed | 83 wt % methanol/ 17 wt % water |
| Pressure, psig | 315 (2273 kPa) |
| Dehydration Rx Inlet Temp., °F. | 600 (315° C.) |
| Conversion Rx Inlet Temp., °F. | 680 (360° C.) |
| Conversion Rx Methanol WHSV | 1.6 |
| Recycle Ratio, mols/mol charge | 9/1 |

TABLE 2

| Effect Of Separator Temperature On Waste Water COD | | | | |
| --- | --- | --- | --- | --- |
| Separator Temp., °C. | 27° C. | 32° C. | 38° C. | 52° C. |
| (°F.) | (81) | (90) | (100) | (126) |
| COD Non-acidic oxygenates, mg O$_2$/l | 2943 | 2252 | 1763 | 1295 |
| COD acids, mg O$_2$/l | 530 | 528 | 537 | 590 |
| Total COD, mg O$_2$/l | 3473 | 2780 | 2300 | 1880 |

Methanol conversion was greater than 99.99% in all cases. As shown in Table 2, increasing the separator temperature from operation at 81° F. to 126° F. (27°–52° C.) decreased the total waste water COD by about 46% i.e.. from 3473 to 1880 mg O$_2$/l. The decrease in non-acidic oxygenate COD of the waste water was even greater, at 56% reduction.

Thus, controlling the product separator temperature in accordance with the process of the present invention can result in a reduced size of the waste water treatment plant necessary for commercial operation of the MTG and MTO processes. Further, since the waste water COD is reduced in the waste water entering the treatment facilities, the potential for environmental discharge of unacceptable quality effluent from the waste water treatment plant is desirably minimized.

Having thus generally described the process of the present invention and discussed specific embodiments in support thereof, it is to be understood that no undue restrictions as to the scope of the present invention are to be imposed by reason thereof.

What is claimed is:

1. In a process for converting lower aliphatic oxygenates to hydrocarbons by contacting the oxygenates with a crystalline zeolite conversion catalyst and wherein a byproduct water effluent stream is produced, the improvement which comprises, regulating the operating temperature of a gaseous-/liquid hydrocarbon/water phase separator from which said byproduct water effluent stream issues in the range of about 50° C. to 100° C. to reduce the total byproduct water chemical oxygen demand.

2. The process according to claim 1, which further comprises regulating the operating pressure of said separator by process regulating means to reduce the total byproduct water chemical oxygen demand.

3. The process according to claim 1, wherein said separator is regulated so as to operate at a constant temperature higher than about 40° C.

4. The process according to claim 2, wherein sad separator pressure is above about 700 kPa.

5. The process according to claim 4, wherein the process is an MTG fixed-bed process, and said separator pressure is at least 900 kPa.

6. The process according to claim 1, wherein said regulating of the separator temperature is conducted by controlling the temperature of effluent stream entering the separator by indirect heat exchange means.

7. The process according to claim 6, wherein the temperature of the effluent stream is regulated by indirectly contacting the stream with recycled gas or cold feed, or using air or water cooling to cool the effluent stream prior to entry into the separator.

8. The process according to claim 1, wherein said oxygenates are $C_1$–$C_4$ oxygenates selected from the group consisting of monohydric alcohols, ethers derived from said alcohols, and mixed ethers derived from said alcohols.

9. The process according to claim 8, wherein said $C_1$–$C_4$ oxygenates are present in conjunction with water as a feed in proportions ranging from about 0 to about 50% by wt.

10. The process according to claim 1, wherein said catalyst is a medium pore size crystalline alumino-silicate zeolite having a silica-to-alumina ratio of at least about 12, a constraint index of about 1 to 12 and significant acid activity.

11. The process according to claim 10, wherein zeolite is selected from the group consisting of ZSM-5, ZSM-11, ZSM-12, ZSM-22, ZSM-23, ZSM-35 and ZSM-48.

12. A continuous process for converting methanol feedstock to liquid hydrocarbons, byproduct water and light gas, comprising the steps of:
 a. contacting the oxygenate feedstock in a fixed bed reaction zone with acid ZSM-5 zeolite catalyst at elevated temperature and pressure under conversion conditions to react more than 99.99% of methanol to produce a hot effluent stream containing $C_5^+$ gasoline range hydrocarbons, light hydrocarbons, and water;
 b. cooling the effluent stream under process pressure to condense a major amount of $C_5^+$ hydrocarbons as a liquid organic phase along with a byproduct water liquid phase containing dissolved organic oxygenate components; and
 c. separating the cooled effluent stream at a temperature greater than 40° C. to 50° C. to reduce concentration of said organic oxygenate components and chemical oxygen demand in the byproduct water phase below about 2000 ppm, while recovering a liquid hydrocarbon stream and a light gas stream.

13. The process of claim 12, wherein separation step (c) is conducted at about 52° C. and a pressure of at least 900 kPa to recover an aqueous phase consisting essentially of water and not more than 1295 ppm non-acidic organic oxygenates.

* * * * *